US009019499B2

(12) United States Patent
Tovey

(10) Patent No.: US 9,019,499 B2
(45) Date of Patent: Apr. 28, 2015

(54) TUNABLE LIGHT SOURCE SYSTEM AND METHOD HAVING WAVELENGTH REFERENCE CAPABILITY

(71) Applicant: Cameron John Tovey, Painted Post, NY (US)

(72) Inventor: Cameron John Tovey, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 218 days.

(21) Appl. No.: 13/628,304

(22) Filed: Sep. 27, 2012

(65) Prior Publication Data

US 2014/0085637 A1    Mar. 27, 2014

Related U.S. Application Data

(60) Provisional application No. 61/541,383, filed on Sep. 30, 2011.

(51) Int. Cl.
| | | |
|---|---|---|
| *G01N 21/25* | (2006.01) | |
| *H01S 3/10* | (2006.01) | |
| *G01J 3/10* | (2006.01) | |
| *H01S 5/0687* | (2006.01) | |
| *G01N 21/39* | (2006.01) | |
| *G01N 21/77* | (2006.01) | |
| *G01J 3/12* | (2006.01) | |

(52) U.S. Cl.
CPC ............... *G01J 3/10* (2013.01); *H01S 5/0687* (2013.01); *G01N 21/39* (2013.01); *G01J 2003/1213* (2013.01); *G01J 2003/1221* (2013.01); *G01N 21/7743* (2013.01)

(58) Field of Classification Search
CPC ................. G01J 2003/1213; G01J 2003/1221; G01J 3/10; G01N 21/7743; G01N 21/39; H01S 5/0683; H01S 5/06832; H01S 5/06835; H01S 5/06837; H01S 5/0687; H01S 3/005
USPC ........ 356/445, 402–425; 362/293; 372/20, 34
See application file for complete search history.

(56) References Cited

U.S. PATENT DOCUMENTS

| | | | | |
|---|---|---|---|---|
| 5,991,477 A | * | 11/1999 | Ishikawa et al. ................ | 385/24 |
| 6,018,535 A | * | 1/2000 | Maeda ............................ | 372/20 |
| 6,094,446 A | * | 7/2000 | Tei et al. ......................... | 372/32 |

(Continued)

OTHER PUBLICATIONS

International Search Report and Written Opinion of International Searching Authority issued Dec. 20, 2012 in corresponding PCT Application No. PCT/US2012/057160, filed Sep. 26, 2012.

*Primary Examiner* — Michael A Lyons
*Assistant Examiner* — Violeta A Prieto
(74) *Attorney, Agent, or Firm* — John L. Haack

(57) ABSTRACT

Tunable light source systems and methods with wavelength reference capability are disclosed. A method includes reference filtering a portion of a tunable light beam while the tunable center wavelength $\lambda_C$ is tuned over a range by adjusting a wavelength tuning parameter x. The method also includes detecting the reference-filtered tunable light beam and generating therefrom at least one detected light spectrum as a function of the tunable center wavelength $\lambda_C$. The method further includes determining a reference wavelength tuning parameter $x_{CR}$ corresponding to a reference tunable center wavelength $\lambda_{CR}$ based on a maximum value of the at least one detected light spectrum.

10 Claims, 12 Drawing Sheets

(56) References Cited

U.S. PATENT DOCUMENTS

| | | |
|---|---|---|
| 6,400,737 B1 | 6/2002 | Broutin et al. |
| 7,199,919 B2 * | 4/2007 | Emori et al. .................. 359/334 |
| 7,424,187 B2 | 9/2008 | Montgomery et al. |
| 7,576,333 B2 | 8/2009 | Caracci et al. |
| 7,599,055 B2 | 10/2009 | Gollier et al. |
| 8,384,905 B2 * | 2/2013 | Wu ................................ 356/445 |
| 8,670,121 B1 * | 3/2014 | Pastel et al. ................... 356/416 |
| 2005/0013000 A1 * | 1/2005 | Uehara ........................ 359/586 |
| 2005/0134861 A1 | 6/2005 | Kringlebotn et al. |
| 2006/0205058 A1 | 9/2006 | Frutos et al. |
| 2007/0195320 A1 * | 8/2007 | Sriram et al. ................. 356/301 |
| 2007/0202543 A1 | 8/2007 | Gollier et al. |
| 2007/0211245 A1 | 9/2007 | Pastel et al. |
| 2008/0089699 A1 * | 4/2008 | Li et al. ......................... 398/197 |
| 2009/0154509 A1 * | 6/2009 | Suzuki et al. .................. 372/22 |
| 2010/0157295 A1 * | 6/2010 | Ko et al. ........................ 356/326 |
| 2010/0296089 A1 | 11/2010 | Webb et al. |
| 2010/0303107 A1 * | 12/2010 | Bhatia et al. ................... 372/20 |
| 2011/0109909 A1 | 5/2011 | Wu |
| 2013/0093335 A1 * | 4/2013 | Vinkenvleugel et al. ...... 315/158 |
| 2014/0071450 A1 * | 3/2014 | Pastel et al. ................... 356/416 |

* cited by examiner

TUNABLE LIGHT SOURCE SYSTEM AND METHOD HAVING WAVELENGTH REFERENCE CAPABILITY

CROSS-REFERENCE TO RELATED APPLICATIONS

This application claims the benefit of priority under 35 U.S.C. §119 of U.S. Provisional Application Ser. No. 61/541,383, filed Sep. 30, 2011, the content of which is relied upon and incorporated herein by reference in its entirety.

The entire disclosure of any publication or patent document mentioned herein is incorporated by reference.

FIELD

The present disclosure relates to tunable light sources, and in particular to tunable light source systems for label-independent optical readers where the tunable light source system can provide a wavelength reference.

BACKGROUND

Label-independent detection (LID) optical readers can be used, for example, to detect drug binding to a target molecule such as a protein, or changes in living cells as material within a cell is displaced in response to a drug. Certain types of LID optical readers measure changes in the refractive index on the surface of a resonant waveguide grating (RWG) biosensor for an array of RWG biosensors. The individual RWG biosensors are located in respective wells of a microplate.

In one type of LID optical reader, narrowband light is swept over a range of wavelengths and directed to each RWG biosensor using a narrow-band tunable light source. To ensure accurate RWG biosensor measurement, the center wavelength of the narrowband light must be known to a high degree of resolution with respect to the particular wavelength tuning parameter used to tune the center wavelength. To date, achieving such high resolution has proven to be very expensive. Alternative systems and methods are needed for cost-effective wavelength tuning that can be referenced to a reference wavelength while also meeting high-resolution requirements with respect to the wavelength tuning parameter.

SUMMARY

An aspect of the disclosure is a tunable light source system that provides a reference to a wavelength tuning parameter. The system includes a tunable light source that emits a tunable light beam having a tunable center wavelength $\lambda_C$ based on a wavelength tuning parameter x. The tunable light source generates an electrical signal representative of the wavelength tuning parameter. The system further includes a light-deflecting element disposed in the tunable light beam to deflect at least a portion of the tunable light beam. The system also has a reference filter having a reference bandwidth. The reference filter is disposed so that it filters the deflected portion of the tunable light beam to form a filtered light beam. The system further includes at least one photodetector arranged to detect the filtered light beam and generate at least one detector electrical signal representative of at least one detected light spectrum. The filtered light beam can include transmitted and reflected light beams formed by at least one of transmission and reflection from the reference filter, and two photodetectors can be used to detect the reflected and transmitted filtered light beams. The system also has a controller operably connected to the tunable light source and the photodetector. The controller can be configured to receive the wavelength-tuning-parameter electrical signal and the at least one detector electrical signal and determine a reference wavelength tuning parameter $x_{CR}$ corresponding to a reference tunable center wavelength $\lambda_{CR}$ based on a maximum value of the detected light spectrum.

Another aspect of the disclosure is a method of establishing a reference to a wavelength tuning parameter x of a tunable light source. The method includes reference-filtering a portion of a tunable light beam having a tunable center wavelength $\lambda_C$ while the tunable center wavelength $\lambda_C$ is tuned by adjusting the wavelength tuning parameter x. The method also includes detecting the reference-filtered tunable light beam and generating therefrom at least one detected light spectrum as a function of the tunable center wavelength $\lambda_C$. The method further includes determining a reference wavelength tuning parameter $x_{CR}$ corresponding to a reference tunable center wavelength $\lambda_{CR}$ based on a maximum value of the at least one detected light spectrum.

These and other aspects of the disclosure will be further understood and appreciated by those skilled in the art by reference to the following written specification, claims and appended drawings.

BRIEF DESCRIPTION OF THE DRAWINGS

A more complete understanding of the present disclosure can be had by reference to the following detailed description when taken in conjunction with the accompanying drawings, where.

DETAILED DESCRIPTION

Reference is now made to embodiments of the disclosure, exemplary embodiments of which are illustrated in the accompanying drawings.

Figure 1:
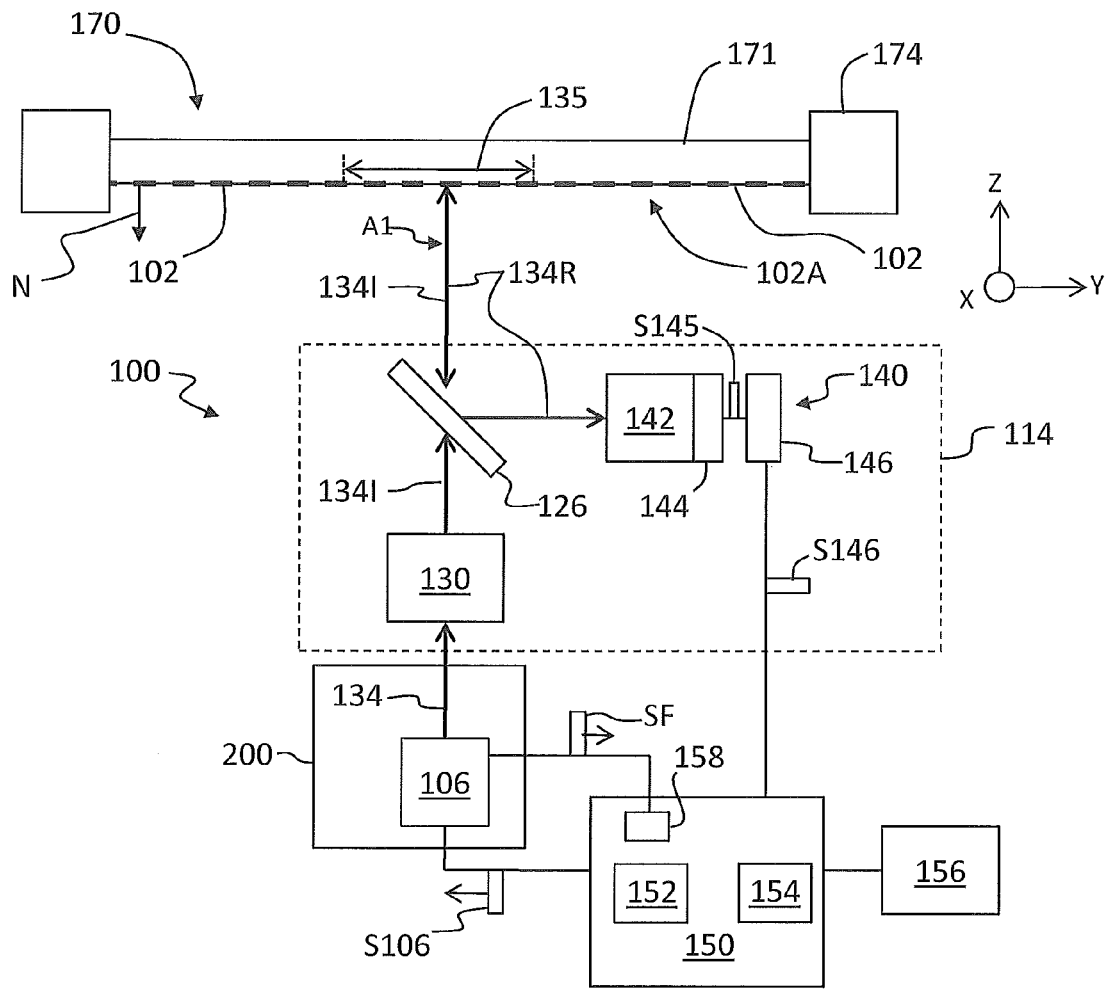
FIG. 1 is a generalized schematic diagram of an example optical reader system that includes the tunable light source system of the disclosure.

FIG. 1 is a generalized schematic diagram of an example optical reader system ("system") 100 suitable for use with the tunable light source systems and methods disclosed herein and described in greater detail below. The system 100 includes an imaging system 114 that is used to interrogate one or more resonant waveguide grating (RWG) biosensors 102. The imaging system 114 includes an illumination optical system 130 and an optical imager ("optical imager") 140. Example imaging systems 114 are discussed in greater detail below. Example optical reader systems 100 with tunable light sources are disclosed in U.S. Patent Application Publications No. US2011/0109909 and US2010/0296089.

Figure 2:
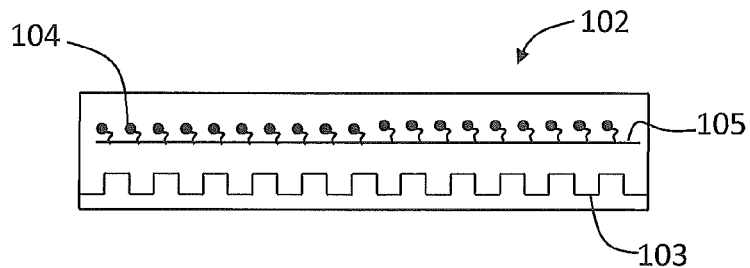
FIG. 2 is a close-up schematic view of an example RWG biosensor.
Figure 3:
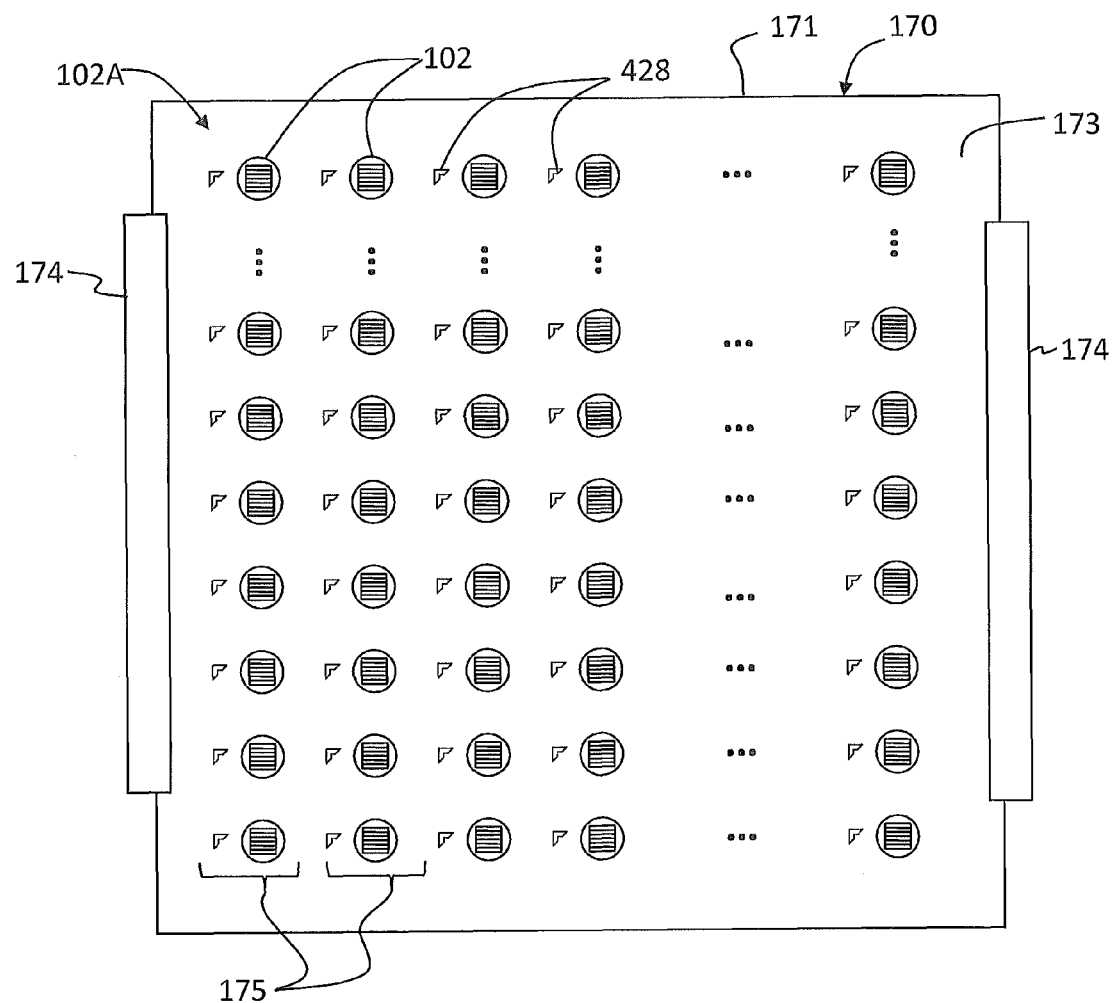
FIG. 3 is a face-on view of an example microplate that operably supports an array of RWG biosensors in associated regions or "wells," with the microplate being held by a microplate holder.
Figure 4:
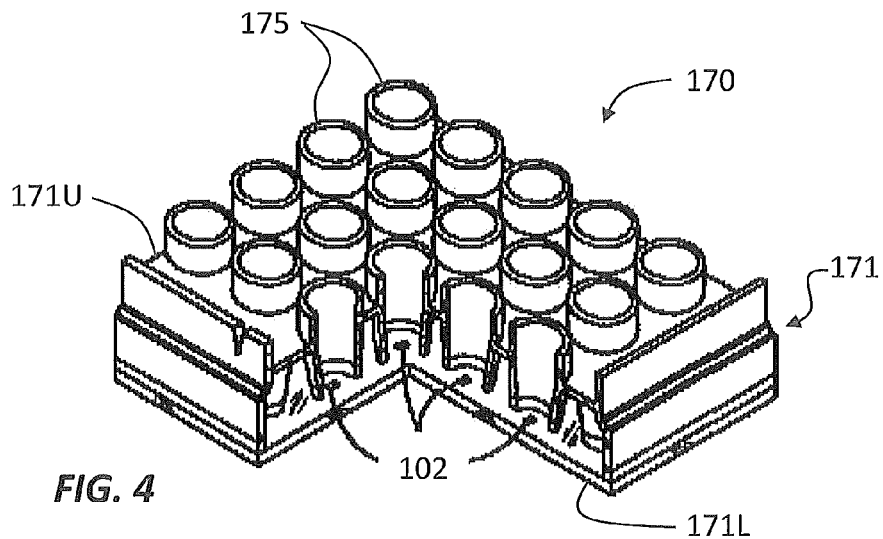
FIG. 4 is a cut-away perspective view of a portion of an example microplate.

FIG. 2 is a close-up schematic side view of an exemplary RWG biosensor 102, which has a grating 103 and a surface 105 configured so that a select biological substance 104 affixes thereto. The RWG biosensors 102 need to be supported so that they can be optically interrogated. The typical support structure is called a "microplate." FIG. 3 is a face-on view of an example microplate 170 that comprises a support plate 171 with a surface 173 having a plurality of wells 175 formed therein. An example support plate 171 has a two-part construction of an upper plate 171U and a lower plate 171L, as shown in the partial view of FIG. 4 and as described, for example, in U.S. Patent Application Publication No. 2007/0211245.

The microplate 170 of FIG. 3 illustrates an exemplary configuration where RWG biosensors 102 are arranged in an array 102A and operably supported in wells 175. An exemplary RWG biosensor array 102A has a 4.5 mm pitch for RWG biosensors 102 that are 2 mm square, and includes 16 RWG biosensors per column and 24 RWG biosensors per row. In embodiments, fiducials 428 are used to position and/or align microplate 170 in system 100. A microplate holder 174 is also shown holding microplate 170. Many different types of plate holders can be used as microplate holder 174.

With reference again to FIG. 1, system 100 includes a tunable light source system 200 that is described in greater detail below. The tunable light source system 200 includes a tunable light source 106. The tunable light source 106 is configured to generate a narrow-wavelength tunable light beam 134 having a spectral bandwidth and a predetermined sequence of distinct central wavelengths $\lambda_C$ over a predetermined time period. In embodiments, tunable light source 106 is configured to emit a time-series of narrow-band tunable light beams 134 having respective central wavelengths $\lambda_C$ ranging from 838 nm to 853 nm at a tuning speed of 0.1 nm/sec to 300 nm/sec. The time-series of narrow-band tunable light beams ("tunable light beams") 134 can also be thought of as a single narrow-band light beam whose center wavelength $\lambda_C$ varies with time. Although tunable light source 106 is shown emitting tunable light beam 134 into free space, guided-wave configurations that use optical waveguides (e.g., optical fibers) can also be selected.

The tunable light beam 134 from tunable light source 106 passes to imaging system 114 and to illumination optical system 130, which has an associated optical axis A1. The illumination optical system 130 transforms tunable light beam 134 into at least one incident optical beam ("incident light") 134I. The incident optical beam 134I passes through a beam splitter 126 and is incident over an area 135 of microplate 170, wherein area 135 includes one or more RWG biosensors 102 (e.g., over 4×3 wells of a 384 well-formal microplate 170, over just one RWG biosensor, or over all of the RWG biosensors). In one example, incident optical beam 134I is moved (scanned) over RWG biosensor 102 to cover different areas 135 by either moving (scanning) illumination optical system 130 or by moving microplate 170 via microplate holder 174.

The incident optical beam 134I reflects from the one or more RWG biosensors 102, thereby forming a reflected optical beam 134R (i.e., reflected light). The reflected optical beam 134R is directed by beam splitter 126 to an optical imager 140 having an imaging lens 142 and an image sensor 144 that captures an electronic (i.e., digital) image 145 (see FIG. 5) of the illuminated area 135 that includes the one or more RWG biosensors 102. The image sensor 144 generates a raw electronic image signal S145 representative of the captured electronic image 145. The optical imager 140 also includes image-sensor electronics 146 that pre-processes raw electronic image signals S145 from image sensor 144 and generates a pre-processed electrical image signal S146 representative of the pre-processed digital image. An example image sensor 144 is a charge-coupled device (CCD) chip such as the KAI-0340 CCD chip with a pixel size of 7.4 microns, available from Kodak, Inc., Rochester, N.Y., or a complementary metal oxide semiconductor (CMOS) chip. An example optical imager 140 is a CCD camera such as the Prosilica GE680 GigE camera, available from Prosilica, Burnaby, British Columbia, Canada, which camera has a maximum frame rate of 215 fps at VGA resolution. In embodiments, image sensor 144 can be an array of one or more photodiodes.

The system 100 also includes a controller 150 having a processor unit ("processor") 152 and a memory unit ("memory") 154. Example processors 152 include a computer, microprocessor, one or more central-processing units (CPU), a field-programmable gate array (FPGA) or the like. The memory 154 can be any type of digital memory used in computers, such as solid-state memory, magnetic memory and optical memory. The controller 150 receives pre-processed electrical image signal S146 from image-sensor electronics 146 and stores it in memory 154. The processor 152 analyzes digital images 145 embodied in pre-processed electrical image signals S146 based on instructions (e.g., image-processing software) stored therein or in memory 152. This process is discussed in greater detail below.

In embodiments, controller 150 includes or is operably connected to a display unit 156 that displays measurement information such as spectra plots, resonant wavelength plots and other measurement results, as well as system status and performance parameters. In embodiments, the spectra can be processed directly so that only the resonant wavelengths (as calculated, for example, as the respective centroids of measured spectra) are stored in memory 154.

In an example, controller 150 also includes a data acquisition card 158 that is electrically connected to tunable light source 106 and that receives a feedback signal SF from the tunable light source that includes information about a wavelength tuning parameter x, as discussed in greater detail below.

Example RWG biosensors 102 make use of changes in the refractive index at sensor surface 105 that affect the waveguide coupling properties of incident optical beam 134I and reflected optical beam 134R to enable label-free detection of biochemical substance 104 (cells, molecules, proteins, drugs, chemical compounds, nucleic acids, peptides, carbohydrates, etc.) on the RWG biosensor. The biochemical substance 104 may be located within a bulk fluid deposited on RWG biosensor surface 105, and the attachment of this biochemical substance to the biosensor surface alters the index of refraction at the RWG biosensor 102.

To detect biochemical substance 104, RWG biosensor 102 is probed with incident optical beam 134I, and reflected optical beam 134R is received at optical imager 140. The optical imager 140 is synchronized with tunable light source 106 so that as the center wavelength $\lambda_C$ of incident optical beam 134I is swept (tuned) over the wavelength band, the optical imager captures a series of digital images 145 corresponding to the different wavelengths. Thus, optical imager 140 obtains a sequence or series ("collection") 147 of RWG biosensor images 145, each of which corresponds to an incident optical beam 134I with a distinct center wavelength $\lambda_C$.

Figure 5:
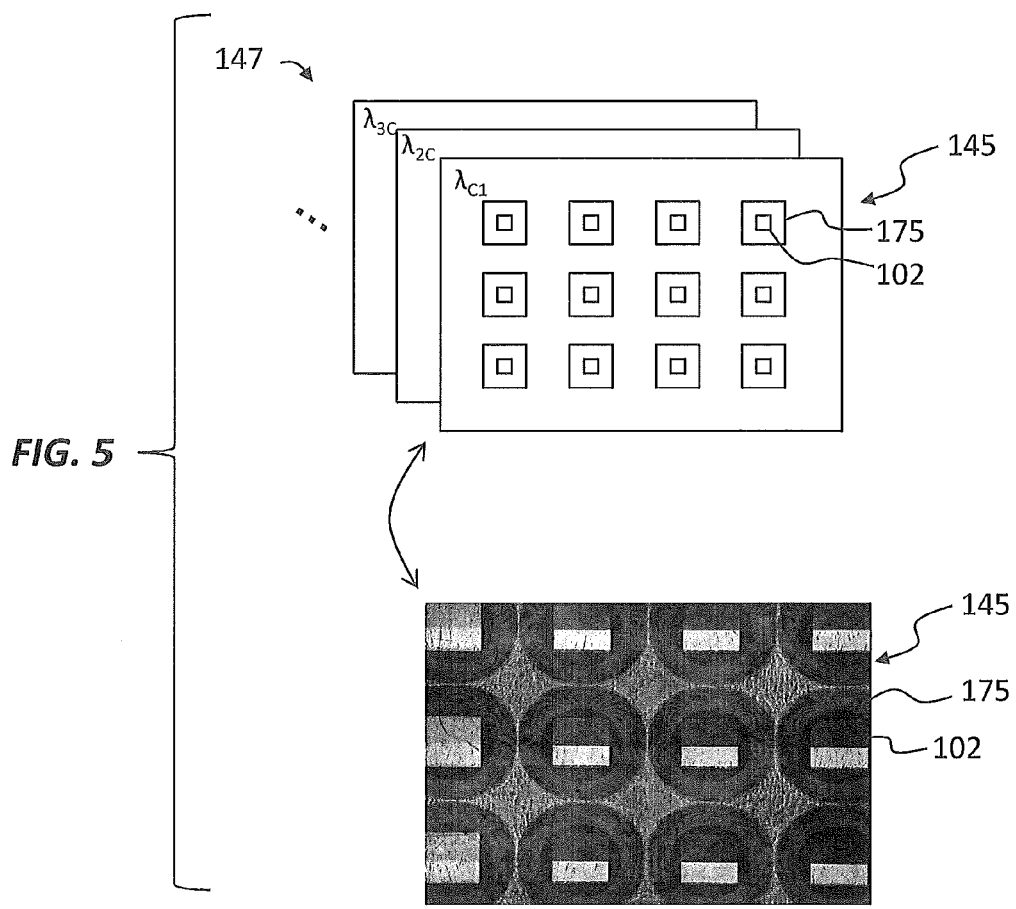
FIG. 5 is a schematic diagram illustrating a collection of digital images associated with different wavelengths of incident illumination provided by the tunable light source system.

FIG. 5 schematically illustrates the collection 147 of images 145 for different (central) wavelengths $\lambda_{C1}, \lambda_{C2}, \ldots \lambda_{Cj} \ldots \lambda_{Cn}$, which collection constitutes a "three-dimensional" (3D) data file or "data cube" of images. FIG. 5 also includes an example of an actual image 145. The optical imager 140 takes a sequence or series of images or pictures 145 of RWG biosensor(s) 102, where each image corresponds to one of the distinct central wavelengths $\lambda_C$ of the series of tunable light beams 134 emitted from tunable light source 106. Lastly, processor 152 receives and processes image collection 147 to determine, for example, whether there was a biochemical interaction or other event on one or more of RWG biosensors 102.

The controller 150 is configured (e.g., processor 152 is programmed or operates under the control of software stored in memory 154) to detect changes (e.g., on the order of 1 part per million) in the RWG biosensor 102 refractive index caused by the presence of biological substance 104. In embodiments, RWG biosensor surface 105 can be coated with, for example, biochemical compounds (not shown), or like biologically or chemically active materials, that allow surface attachment only of specific complementary biochemical substances 104 such as antibodies or proteins, thereby enabling RWG biosensor 102 to be both highly sensitive and highly specific. In this way, system 100 and RWG biosensor 102 can be used to detect a wide variety of biological substances 104. Likewise, RWG biosensor 102 can be used to detect the movements or changes in cells immobilized to RWG biosensor surface 105; for example, when the cells move relative to the RWG biosensor or when they incorporate or eject material, a refractive index change occurs.

If multiple RWG biosensors 102 are operably supported in array 102A in wells 175 of microplate 170, which in turn is supported by microplate holder 174, then they can be used to enable high-throughput drug or chemical screening studies. For a more detailed discussion about the detection of a biological substance 104 (or a biomolecular binding event) using scanning optical reader systems 100, see U.S. patent application Ser. No. 11/027,547. Other optical reader systems 100 are described in U.S. Pat. Nos. 7,424,187, 7,599,055, and 7,576,333, and U.S. Patent Application Publications No. 2006/0205058 and 2007/0202543.

The controller 150 and memory 154 therein receive collected pre-processed images 145 via pre-processed electronic image signals S146 for each central wavelength $\lambda_C$ in incident optical beam 134I, with image collection 147 forming the aforementioned "data cube" shown in FIG. 5. The processor 152 then uses image processing software to automatically process the image collection 147 to, for example: 1) determine whether there was a biochemical interaction or other event on one or more of the illuminated RWG biosensor(s) 102; 2) locate sensor region(s) or reference region(s), or both, on each of the illuminated RWG biosensor(s) 102; 3) remove defect regions on each of the illuminated RWG biosensor(s) 102; 4) calibrate a uniformity of surface chemistry and target molecule immobilizations on each of the illuminated RWG biosensor(s) 102; or a combination thereof.

If desired, processor 152 can bin together multiple imaging regions (pixels) with prior knowledge about the locations of sensor and reference regions (not shown) on RWG biosensors 102. In this mode, multiple pixels are grouped together as a single detector and the number of sensor spectra/images can be reduced to the number of binned regions. In this way, the data processing can be greatly simplified.

To achieve a data rate of 1 Hz for a specific interrogation application, the sequential scanning of tunable light source 106 and the sequential acquisition of the spectral images 145 captured by optical imager 140 needs to be completed in 1 second. This requirement is well within the current capability of tunable light source 106 and tunable light source system 200. Of course, to meet this capability or any other data rate, the number of desired wavelength sampling points dictates the frame rate of image sensor 144 (and associated image-sensor electronics 146). For example, to obtain 500 wavelength samples during a single tuning sequence, the frame rate needs to be as fast as 500 frames per second (fps). An optical imager 140 in the form of a CMOS camera, such as the Basler A504k, is able to deliver 500 fps at a full 1024×1280 pixel format, with a higher frame rate being possible for partial-area images. In an application where it is not necessary to achieve a 1 Hz data rate, a slower optical imager 140 can be used.

Example Imaging Systems

Figure 6:
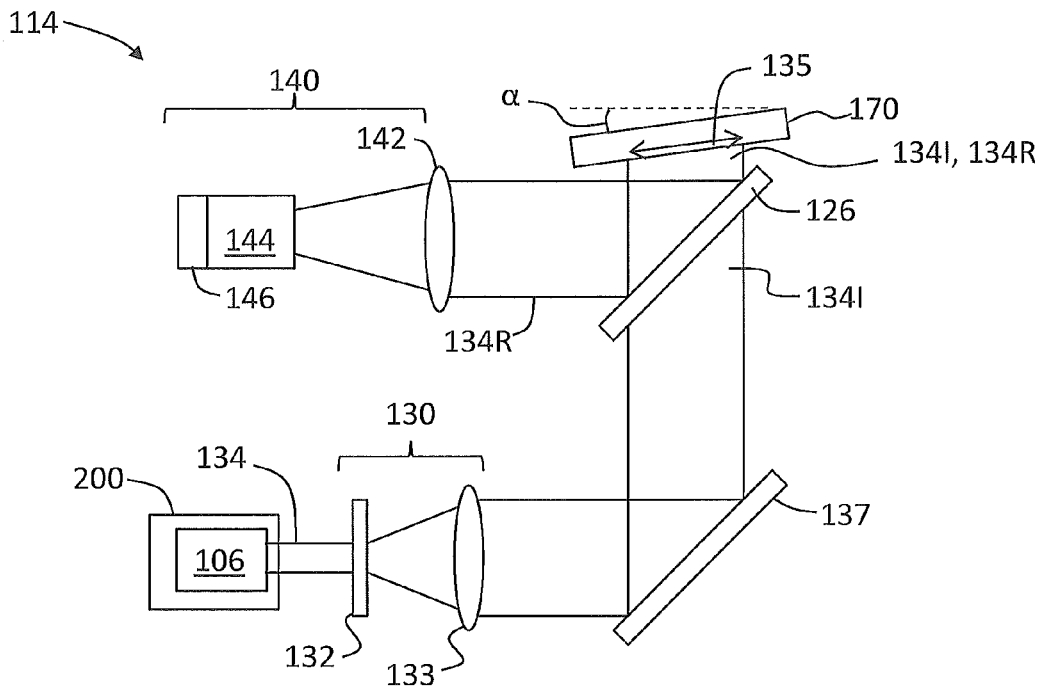
FIG. 6 through FIG. 9 illustrate different embodiments of an optical imager of the optical reader system of FIG. 1.

Four exemplary imaging systems 114 and their operation are now discussed with respect to FIG. 6 through FIG. 9. In FIG. 6, the imaging system 114 has a normal to near-near normal incident angle α at microplate 170, where the illumination optical system 130 includes a lens 132 that receives tunable light beam 134 and directs it towards a collimating lens 133. The collimating lens 133 forms from tunable light beam 134 collimated beam 134I that serves as an interrogation beam, and directs this beam toward a fold mirror 137. The fold mirror 137 reflects collimated interrogation beam 134I such that it travels through beam splitter 126 and illuminates a predetermined number of RWG biosensors 102 located within the wells 175 of microplate 170 over area 135. Alternatively, illumination optical system 130 is configured to form multiple interrogation beams 134I, where each interrogation beam illuminates a corresponding RWG biosensor 102 located within one of the wells 175 of microplate 170. In addition, the optical imager 140 has a telecentric imaging lens 142 with a field of view selected to collect an image 145 from the illuminated RWG biosensor(s) 102.

Figure 7:
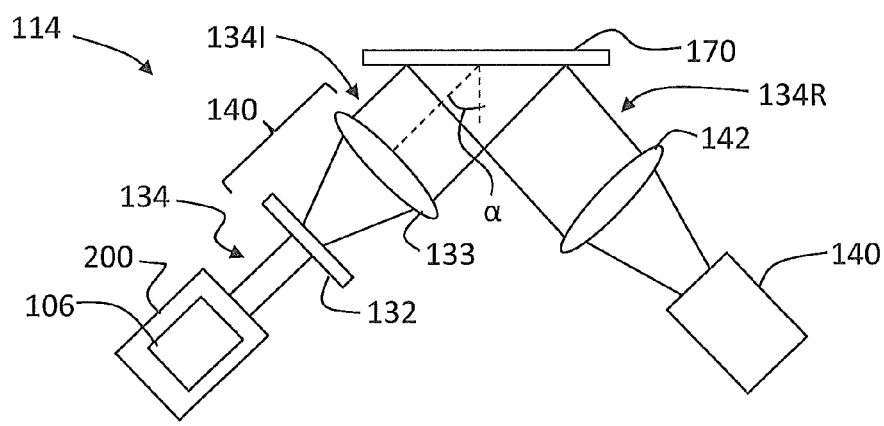

FIG. 7 is a schematic diagram of an example imaging system 114 wherein incident optical beam 134I has an oblique (i.e., non-normal) incidence angle α. The non-normal incidence angle α eliminates the need for beam splitter 126 and can improve the optical efficiency by a factor of four. In this embodiment, illumination optical system 130 includes lens 132 that receives tunable light beam 134 and directs it at a predetermined angle toward collimating lens 133. The collimating lens 133 receives tunable light beam 134 and outputs collimated interrogation beam 134I that illuminates a predetermined number of RWG biosensors 102 located within wells 175 of microplate 170. Alternatively, the illumination optical system 130 can be configured to form multiple interrogation beams 134I, where each interrogation beam illuminates a corresponding RWG biosensor 102. In addition, optical imager 140 has a telecentric imaging lens 142 positioned at a predetermined angle and having a field of view selected to collect an image 145 from the illuminated RWG biosensor(s) 102.

Figure 8:
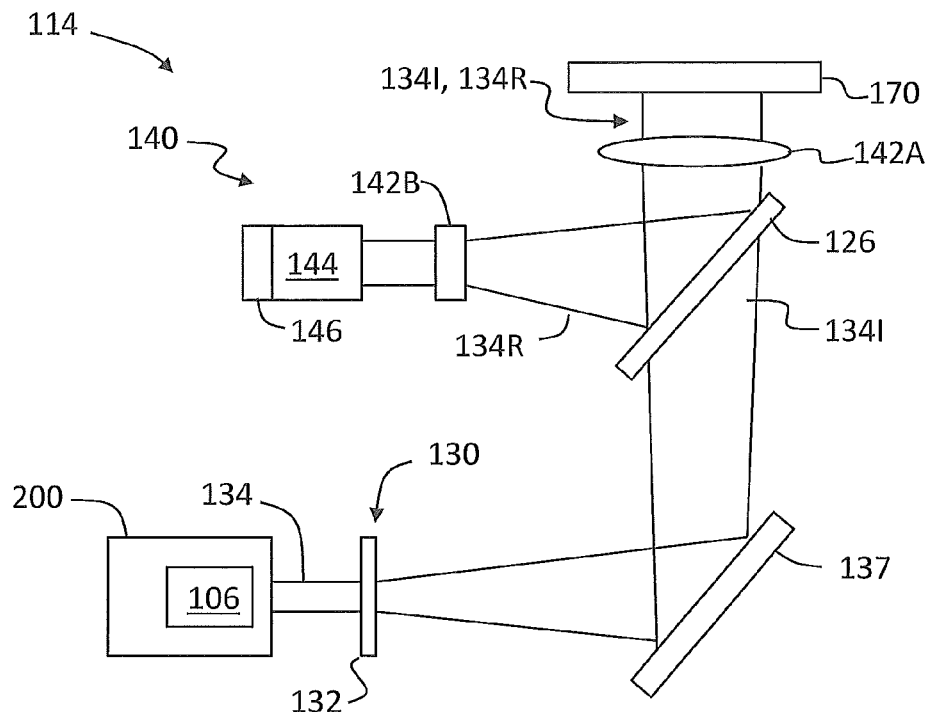

Referring to FIG. 8, there is shown an exemplary imaging system 114 having a relatively small footprint because the illumination optical system 130 and the optical imager 140 share a front lens (or lens group) 142A of telecentric imaging lens 142. In this embodiment, lens 132 of illumination optical system 130 receives tunable light beam 134 and directs it in a diverging manner to fold mirror 137. The fold mirror 137 reflects divergent tunable light beam 134 such that it travels through beam splitter 126 and to front lens 142A. The front lens 142A forms interrogation beam 134I that illuminates a predetermined number of biosensors 102 located within wells 175 of microplate 170. The front lens 142A also collects reflected light 134R and directs it to beam splitter 126. The beam splitter 126 directs reflected light 134R toward a lens 142B, which images reflected light 134R onto image sensor 144 as discussed above.

Figure 9:
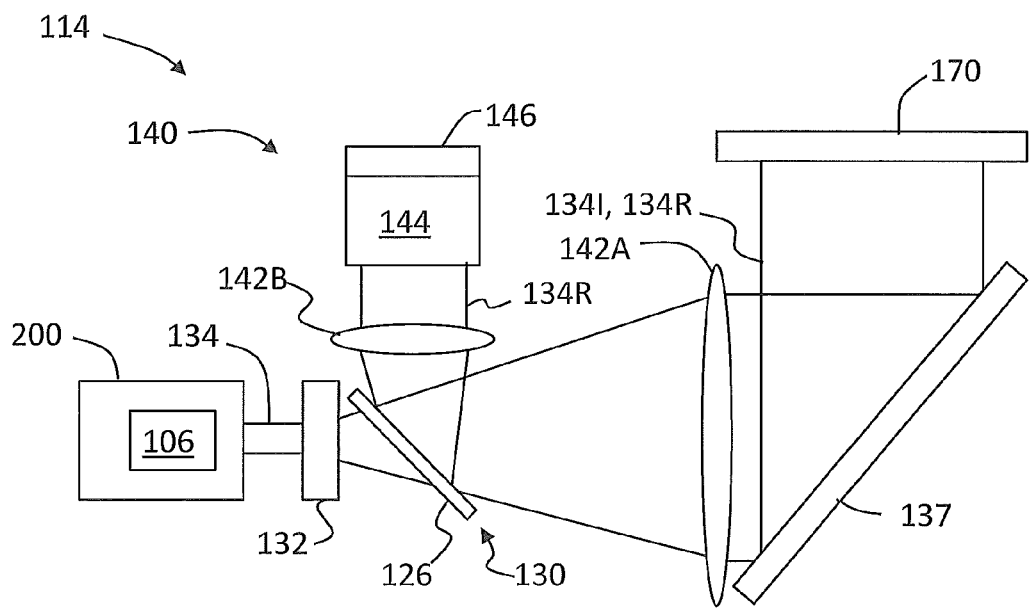

FIG. 9 is a schematic diagram of an example imaging system 114 where the illumination optical system 130 and the optical imager 140 share front lens 142A of telecentric imaging lens 142. The lens 132 of illumination optical system 130 receives tunable light beam 134 and directs it through beam splitter 126 toward front lens 142A via fold mirror 137. The front lens 142A collimates tunable light beam 134 and forms interrogation beam 134I. The front lens 142A also collects reflected light 134R from microplate 170 and RWG biosensors 102 therein and directs it back to beam splitter 126 via fold mirror 137. The beam splitter 126 then directs reflected light 134R to second lens 142B of optical imager 140 and images reflected light 134R onto image sensor 144 as discussed above.

Tunable Light Source System with Wavelength Reference Capability

Figure 10A:
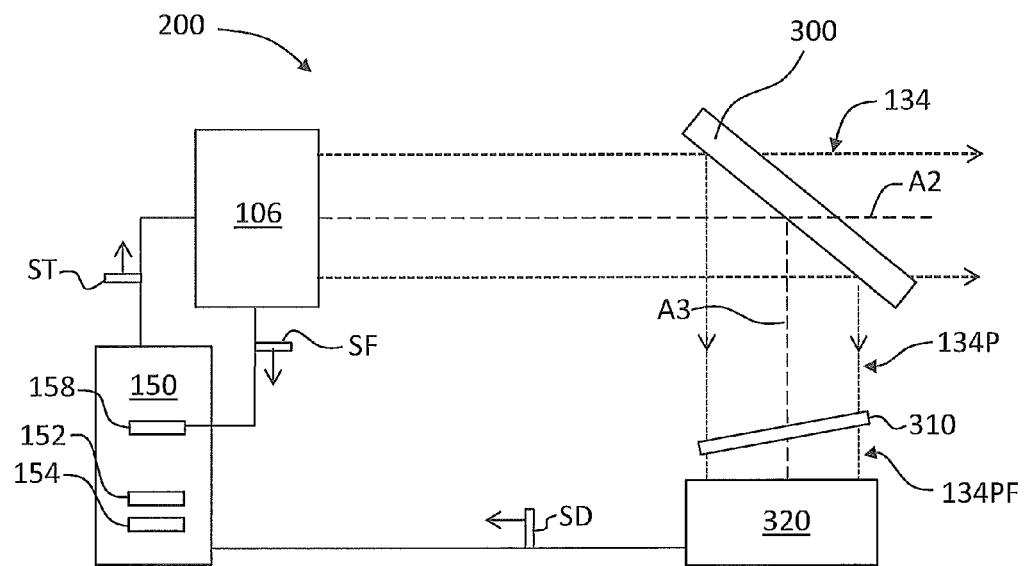
FIG. 10A and FIG. 10B are schematic diagrams illustrating example embodiments of a tunable light source system with wavelength reference capability according to the disclosure.

FIG. 10A is a schematic diagram of an example tunable light source system 200 that is configured to provide a wavelength reference, including, in an example, an absolute wavelength reference. The tunable light source system 200 includes tunable light source 106 operably connected to controller 150. The tunable light source 106 emits tunable light beam 134 along an optical axis A2. The tunable light beam 134 has the aforementioned tunable center wavelength $\lambda_C$ and, in an example, has a spectral width $\Delta\lambda_T$ and a spectral shape that both stay substantially constant as the center wavelength is tuned (adjusted). In the discussion below, tunable light beam 134 is referred to in the singular even though it can also be thought of as a time-series of beams whose center wavelength $\lambda_C$ varies with time.

The tunable light source system 200 includes a light-deflecting element 300 arranged along or adjacent optical axis A2 and that defines an optical axis A3 that forms an angle (e.g., a right angle) with optical axis A2. In an example, light-deflecting element 300 is a beamsplitter that partially reflects an amount of tunable light beam 134 incident thereon and transmits the rest of the tunable light beam. In another example embodiment illustrated in FIG. 10B, light-deflecting element 300 is a mirror. Generally, light-deflecting element 300 deflects at least a portion of tunable light beam 134. In an example, light-deflecting element 300 can be removed from the path of tunable light beam 134 after a reference measurement has been made.

A reference band-pass filter 310 is arranged along optical axis A3, and a reference photodetector 320 is arranged downstream of the reference band-pass filter also along optical axis A3. The reference band-pass filter 310 has a band-pass filter function $F(\lambda)$ and a band-pass width of $\Delta\lambda_R$. The reference photodetector 320 is electrically connected to a controller, such as controller 150 as shown.

Figure 10B:
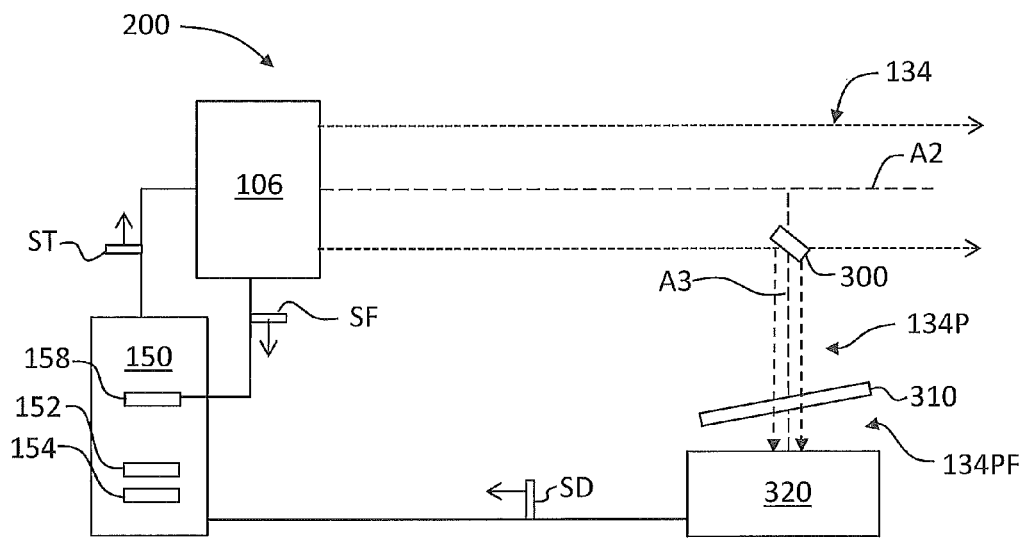

In the operation of tunable light source system 200 of FIG. 10A and FIG. 10B, controller 150 sends a control signal S106 to tunable light source 106 that causes the tunable light source to emit tunable light beam 134. The tunable light source 106 provides controller 150 with feedback signal SF that provides information about a wavelength tuning parameter x used to tune the center wavelength $\lambda_C$ of tunable light beam 134. The wavelength tuning parameter x may be, for example, a mechanical position, a voltage, a current, etc., depending on the type of wavelength tuning mechanism used in tunable light source 106.

The tunable light beam 134 travels along axis A2, and a portion 134P of the tunable light beam is directed by light-deflecting element 300 to travel along axis A3. The tunable light beam portion 134P then travels through reference band-pass filter 310, which forms a filtered light beam portion 134 PF that is detected by photodetector 320. In response, photodetector 320 generates an electrical detector signal SD that is representative of the detected intensity of filtered light beam portion 134 PF as a function of the tuned (i.e., changing) center wavelength $\lambda_C$. The detected intensity is in the form of a detected light spectrum $D(\lambda_C)$, which can also be expressed as a function of the wavelength tuning parameter, i.e., $D(x)$. Thus, electrical detector signal SD is representative of detected light spectrum $D(\lambda_C)$ or $D(x)$. The electrical detector signal SD is then received by controller 150.

Figure 11:
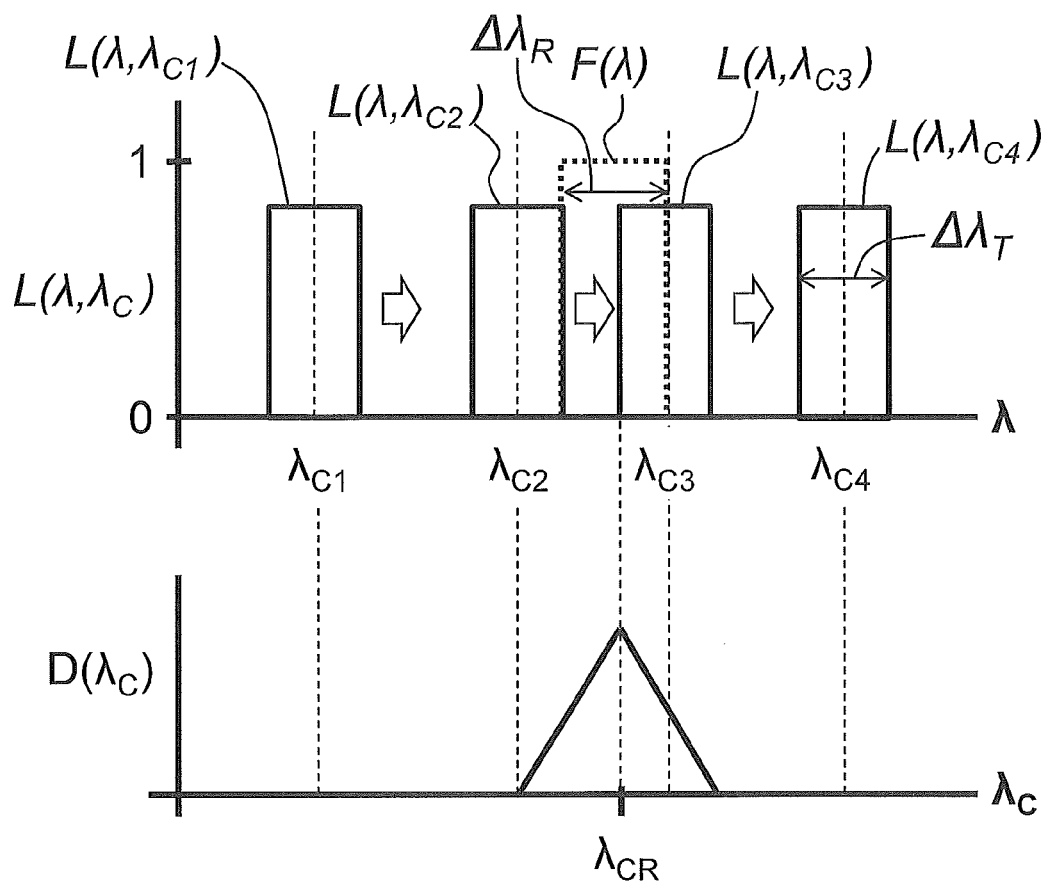
FIG. 11 includes a plot of a series of spectra of the tunable light beam for different center wavelengths relative to a band-pass of a reference filter, and also includes a corresponding plot of the detected light spectrum.

FIG. 11 is a plot of the tunable light beam spectrum $L(\lambda, \lambda_C)$ versus wavelength $\lambda$ for light beam 134 for several different center wavelengths $\lambda_C$ as the wavelength of the tunable light beam is tuned over some wavelength range (e.g., the aforementioned example range of 838 nm to 853 nm). Also shown in the plot is an example reference filter transmission function $F(\lambda)$. The example reference filter transmission function $F(\lambda)$ is shown as having an idealized rectangular form with a transmission of 1 within the band-pass width $\Delta\lambda_R$ and no transmission (i.e., a transmission of 0) outside of the band-pass width. Other forms for filter transmission function $F(\lambda)$, such as Gaussian, Sinc, etc., may also be used, as discussed below.

Also plotted in FIG. 11 is detected light spectrum $D(\lambda_C)$ as a function of center or reference wavelength $\lambda_C$ as detected by reference photodetector 320. The detected light spectrum $D(\lambda_C)$ at a given center wavelength $\lambda_C$ is the product of the tunable light beam spectrum $L(\lambda, \lambda_C)$ of tunable light beam portion 134P and the reference filter transmission function $F(\lambda)$, and over the range of wavelength tuning is given by:

$$D(\lambda_C) = \int_0^\infty d\lambda \cdot L(\lambda, \lambda_C) \cdot F(\lambda)$$

The detected light spectrum $D(\lambda_C)$ depends only on the characteristics of reference band-pass filter 310 as represented by reference filter transmission function $F(\lambda)$ as well as on the properties of tunable light source 106. It does not depend on the particular tuning adjustment mechanism used to tune the tunable light source 106. The center tuning wavelength $\lambda_C$ that corresponds to the maximum in the detected light spectrum $D(\lambda_C)$ is the reference center wavelength $\lambda_{CR}$.

In an example, a spectral interrogation (e.g., with a spectrometer) of tunable light beam 134 from tunable light source 106 is carried out and a comparison to the corresponding peak in the detected light spectrum $D(\lambda_C)$ is performed (e.g., by controller 150) to establish the reference center wavelength $\lambda_{CR}$ as an absolute wavelength reference.

It is noted here that characterization of the forms of $L(\lambda,\lambda_C)$ or $F(\lambda)$ is not required to obtain detected light spectrum $D(\lambda_C)$. Only the detected light spectrum $D(\lambda_C)$ is required to establish the reference wavelength $\lambda_{CR}$, which is established via measurement with tunable light source system 200.

The center wavelength $\lambda_C$ is typically not set directly with tunable light source 106. Rather, it is usually set with some adjustment or offset $\delta x$ with respect to whichever type of wavelength tuning mechanism is employed and its wavelength tuning parameter x. To find a reference setting $x_{CR}$ for tunable light source 106 that corresponds directly to the reference wavelength $\lambda_{CR}$, the wavelength tuning parameter x is adjusted until it corresponds to the peak of the detected light spectrum $D(\lambda_C)$. This value is defined as $x=x_{CR}$. If this setting is disturbed, then the referencing process using spectral interrogation is repeated to establish a new value $x'=x_{CR}$.

Figure 12A:
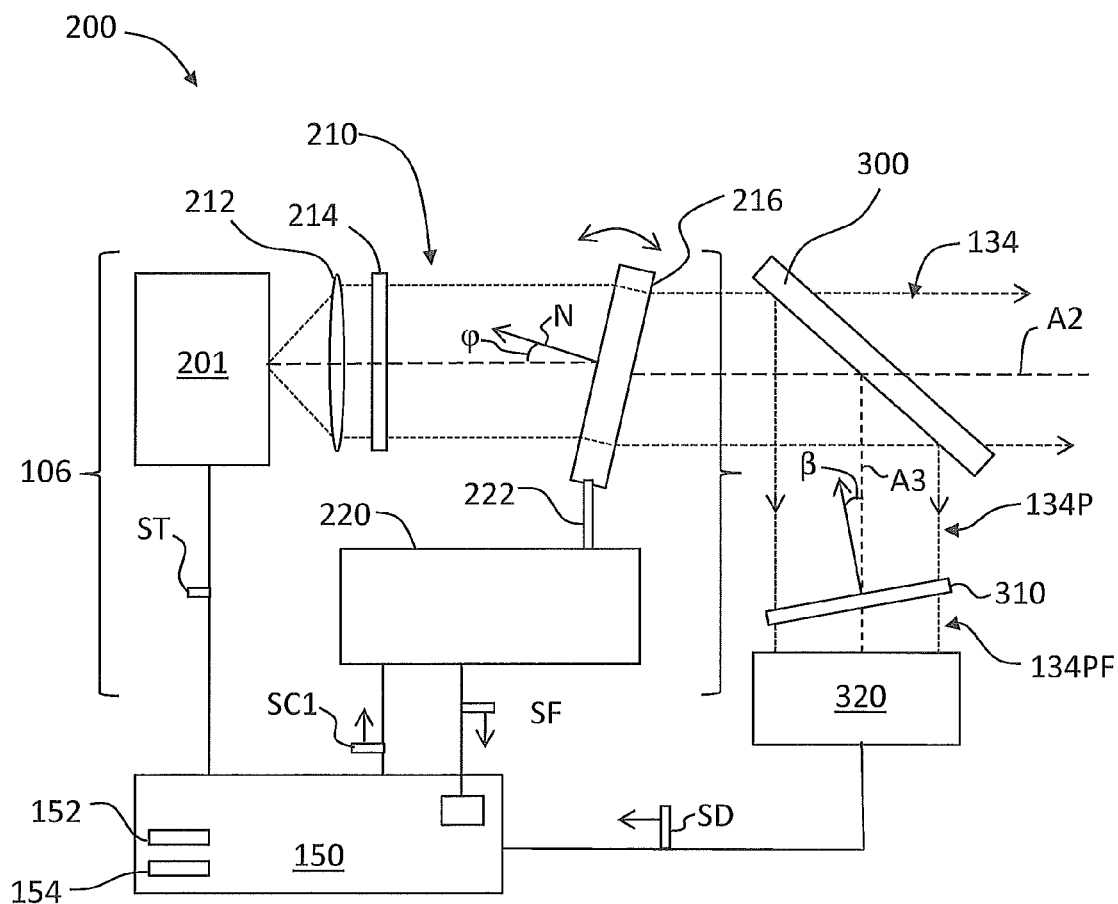
FIG. 12A is a schematic diagram of an example tunable light source system similar to that of FIG. 10A, illustrating an example angle-adjustment unit operably connected to an angle-adjustable filter used to tune the center wavelength of the tunable light beam.

FIG. 12A is similar to FIG. 10A and illustrates an example tunable light source system 200 with an example tunable light source 106. The tunable light source 106 includes a broadband light source 201, such as a superluminescent diode (SLD), as available from Superlum Diodes, Ltd., Moscow, Russia. An example SLD light source 201 has a spectral bandwidth W of 20 nm and a center wavelength $\lambda_C$ of about 840 nm. A conventional broadband LED can also be used as broadband light source 201 provided that the light is sufficiently collimated. The broadband light source 201 emits a broadband light beam 210 along a light source axis A2. In embodiments, broadband light source 201 has a spectral bandwidth in the range of 10 nm to 40 nm.

The tunable light source 106 also includes an angle-adjustable wavelength filter ("filter") 216 arranged downstream of broadband light source 201 along optical axis A2. The filter 216 makes an angle ("filter angle") $\phi$ relative to axis A2 (which is the direction in which collimated broadband light beam 210 travels), and is measured relative to the surface normal N of the filter. The filter 216 is mechanically connected to an angle-adjustment unit 220 configured to control the filter angle $\phi$. Example angle-adjustment units 220 are discussed below.

The filter 216 is configured to transmit light over a spectral band-pass (linewidth) $\Delta\lambda_T$ having a center wavelength $\lambda_C$. The "tunability" of filter 216 refers to its ability to adjust the center wavelength $\lambda_C$ as a function of filter angle $\phi$ while maintaining the spectral linewidth $\Delta\lambda_T$ substantially constant. Thus, the transmission function of filter 216 essentially shifts along with the central wavelength $\lambda_C$. The broadband light beam 210 travels through tunable filter 216 and becomes the aforementioned narrow-band tunable light beam 134 that has a tunable light beam spectrum $L(\lambda, \lambda_C)$ having the aforementioned spectral linewidth $\Delta\lambda_T$. In the case where the spectrum $L(\lambda, \lambda_C)$ of tunable light beam 134 does not change shape but merely shifts along with the center wavelength $\lambda_C$, then the tunable light beam spectrum can be expressed as $L(\lambda-\lambda_C)$.

The tunable light source 106 also preferably includes a polarizer 214 arranged along optical axis A2 between broadband light source 201 and filter 216 to linearly polarize broadband light beam 210 to have P-polarization or S-polarization. In some cases, an S-polarization configuration for polarizer 214 is preferred because it accommodates wider incident beam angles. The tunable light source 106 may also include a collimating lens 212 disposed along optical axis A2 adjacent broadband light source 201.

The filter angle $\phi$ is adjusted by controller 150 sending a control signal SC1 to angle-adjustment unit 220. In response, angle-adjustment unit 220 adjusts the position of filter 216 via adjusting (incrementing) wavelength tuning parameter x to set (increment) the filter angle v. Angle-adjustment unit 220 also sends back to data acquisition board 158 of controller 150 the aforementioned feedback signal SF representative of the wavelength tuning parameter x that provides the filter angle adjustment.

Figure 12B:
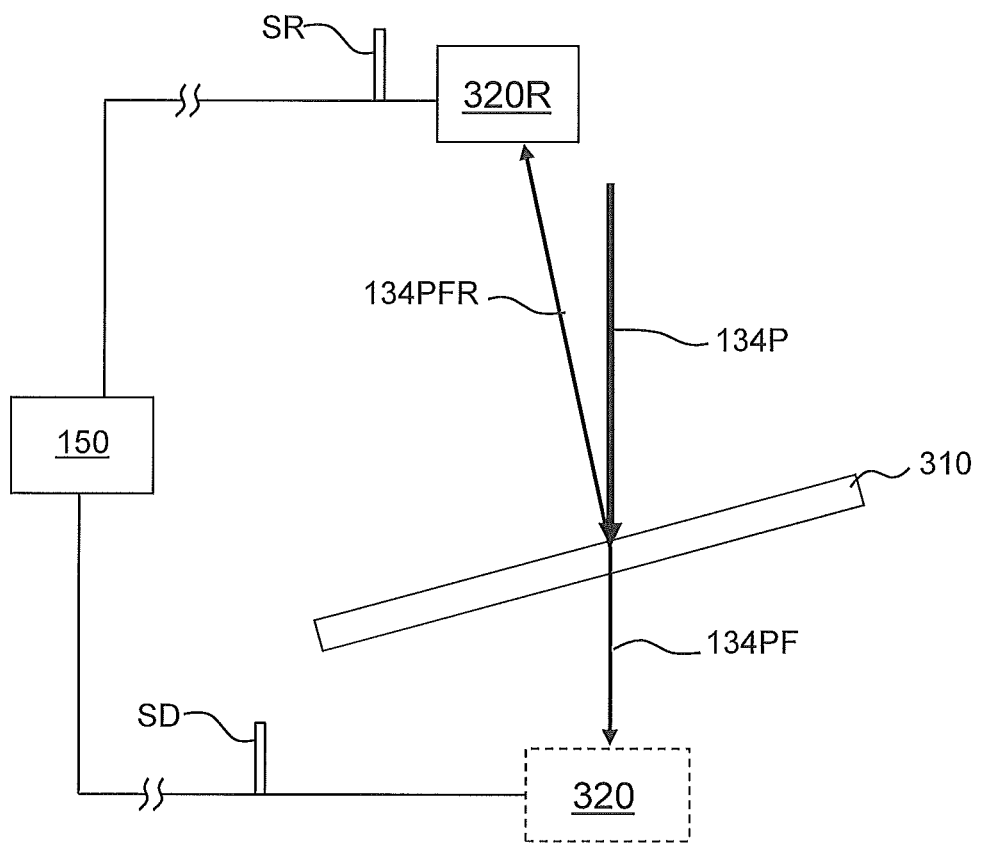
FIG. 12B is a close-up view of tunable light source system illustrating an example embodiment of the detector arrangement that employs either one or two detectors.

FIG. 12B is a close-up view of tunable light source system illustrating an alternative embodiment of the detector arrangement that utilizes either one or two photodetectors. A photodetector 320R can be used to detect reflected light 134 PFR from filter 310 instead of detecting transmitted filtered light 134 PF. In this embodiment, filter 310 functions as a reflective notch filter (i.e., a band-stop filter) with a reflectance spectrum $R(\lambda)$ related to the transmission spectrum $F(\lambda)$ by the equation $F(\lambda) \approx 1-R(\lambda)$. Detector signal SR obtained by reflection shows a "dip" where detector signal SD obtained by transmission shows a peak. The negative of detector signal SR has the same properties as detector signal SD and can be used in peak-finding (e.g., curve-fitting) methods. In a further example, filter 310 may have a notch response in the transmission spectrum, in which case the roles of detectors 320 and 320R are reversed.

In embodiments, both photodetectors 320 (shown in phantom in FIG. 12B) and 320R can be used in combination to respectively detect the transmitted filtered light (beam) 134 PF and reflected filtered light (beam) 134 PFR. In this configuration, filtered light beam 134F can considered to be made up of transmitted filtered light (beam) 134 PF and reflected filtered light (beam) 134 PFR.

In an example, a combined detector signal SN with the essential properties of the original detector SD can be created by combining detector signals SD and SR. In a particular example, detector signals SD and SR can be treated as a differential pair, in which case the combined detector signal becomes:

$$SN = \frac{SD - SR}{SD + SR}$$

This combined detector signal SN has the essential properties of original, single-detector detector signal SD, but is known to have an excellent signal-to-noise ratio (SNR) compared with either detectors signals SD or SR taken alone. In an example, the calculation of combined detector signal SN is carried out in processor 152 of controller 150.

Figure 13:
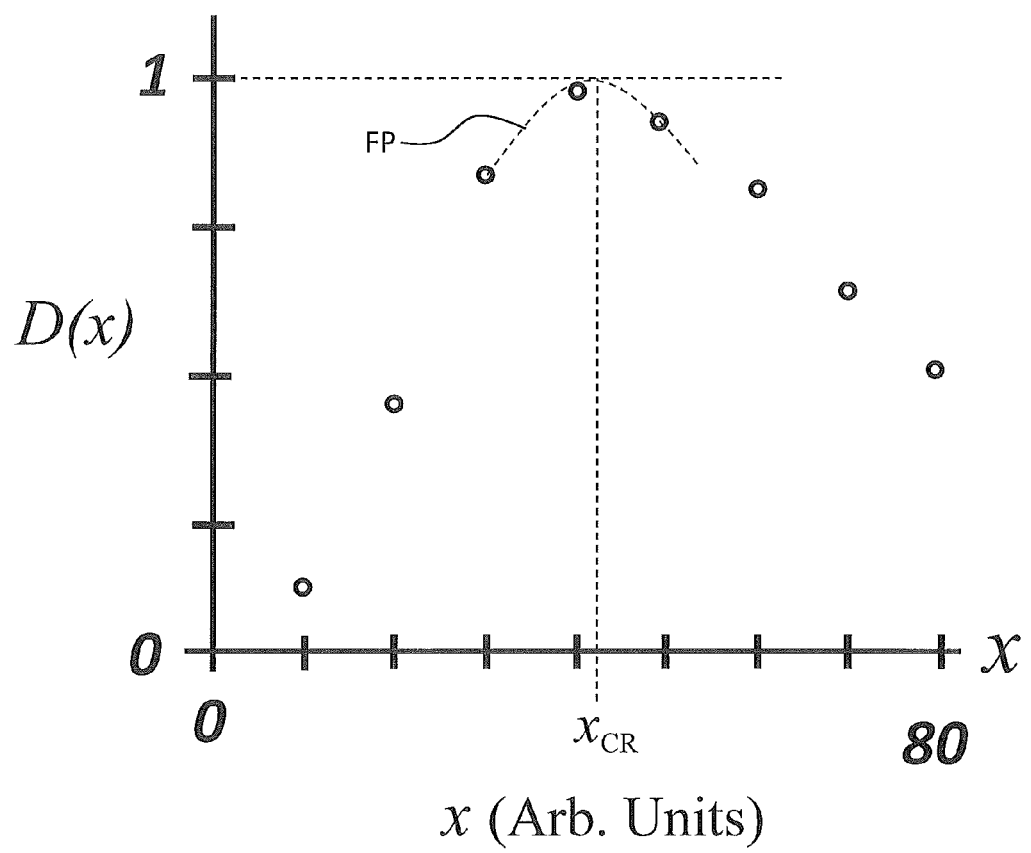
FIG. 13 is a schematic plot of the normalized detected light spectrum D(x) as a function of the wavelength tuning parameter x (arbitrary units), illustrating the use of curve-fitting to establish a reference wavelength tuning parameter $x_{CR}$ from which a reference center wavelength $\lambda_{CR}$ can be determined.

FIG. 13 plots the (normalized) detected light spectrum D(x) (arbitrary units) vs. wavelength tuning parameter x rather than as a function of reference wavelength $\lambda_C$. As the wavelength tuning parameter x is adjusted in discrete steps from 0 to 80, the detected light spectrum D(x) passes through a maximum value of 1 as determined by curve-fitting, such as by a parabolic fit (dashed line PF) using the three data points that include the maximum data point in the (discrete) detected light spectrum D(x). The wavelength tuning parameter x that corresponds to the fitted maximum in detected light spectrum D(x) is the reference wavelength tuning parameter $x_{CR}$, which per the parabolic fitted curve FP has a value of about 42. Other types of curve-fitting (e.g., centroid) can be used to calculate the maximum value of the detected light spectrum D(x). In an example, controller 150 includes instructions embodied in a computer-readable medium that cause the controller to calculate a maximum value in detected light spectrum D(x) or D($\lambda_C$) by curve-fitting. In an example, the data can be filtered for noise before applying the curve-fitting.

This demonstrates that a numerical determination of the peak value of the detected light spectrum D(x) can be found to a much higher resolution (in some cases, orders of magnitude better) than the discrete values available by the particular adjustment mechanism for wavelength tuning parameter x. Very accurate values for the reference center wavelength $\lambda_{CR}$ and for the reference wavelength parameter $x_{CR}$ corresponding thereto can be found by continuously tuning the wavelength of tunable light source 106 while recording detected light spectrum D(x) with reference photodetector 320 to determine reference. Conversion between the reference center wavelength $\lambda_{CR}$ and the reference wavelength tuning parameter $x_{CR}$ is performed based on the aforementioned measured spectral reference.

In an example embodiment of tunable light source system 200, the detector signal SD from reference photodetector 320 is read simultaneously with the reading of biosensor 102 using system 100. At the end of the biosensor 102 scan, there are two sets of measurements: the biosensor measurements and the reference measurements. Both sets of measurements are based on the wavelength tuning parameter x. The biosensor 102 measurements can be analyzed in terms of relative values for the wavelength tuning parameter x while the reference measurements are analyzed to establish an absolute wavelength reference for the wavelength tuning parameter by finding the reference wavelength tuning parameter $x_{CR}$ that corresponds to the reference center wavelength $\lambda_{CR}$. An appropriate correction is then applied to the biosensor 102 measurements. This simultaneous measurement method eliminates the possibility of a drift in the tuning mechanism occurring between a reference measurement and a biosensor 102 measurement.

This simultaneous measurement method can also result in the cancellation of high-order errors that may result from the specific form of the tuning curve of the tunable light source 106 since exactly the same tuning curve was used for the both the biosensor 102 measurement and the reference measurement.

Figure 14:
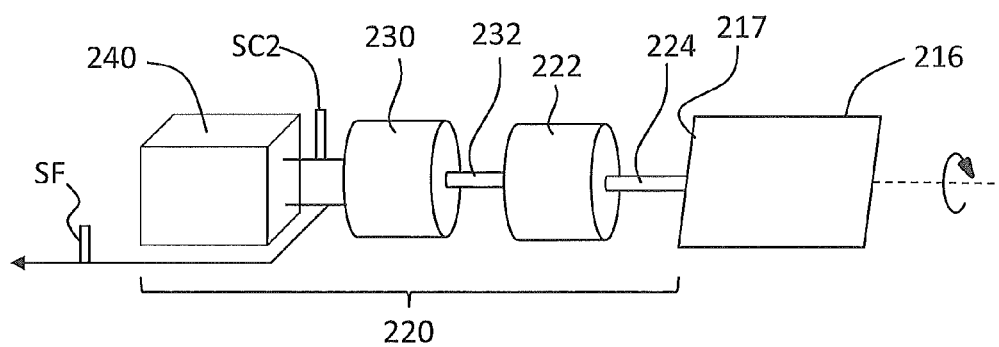
FIG. 14 is a schematic side elevation view of an example angle-adjustment unit that includes a gear box, a motor and a motor controller.

FIG. 14 is a schematic side elevation view of an example angle-adjustment unit 220 that includes a gear box 222 with a drive shaft 224 operably connected to filter 216 at a side 217. The angle-adjustment unit 220 also includes a motor 230 mechanically connected to gear box 222 via a drive shaft 232. The angle-adjustment unit 220 further includes a motor controller 240 electrically connected to motor 230. In an example, motor 230 provides wavelength tuning parameter x in the form of "clicks" or encoder lines per revolution, with each click corresponding to a discrete positional (rotational) increment of drive shaft 232. Further, gear box 222 has a gear ratio R that in an example is relatively high (e.g., R≥1,000) so that it greatly expands the number of clicks per revolution of drive shaft 224 of the gear box.

An example motor 230 suitable for use in angle-adjustment unit 220 is the model 1524-SR brushed DC motor containing a model IE-512 quadrature encoder both from Dr. Fritz Faulhaber GmbH & Co. KG of Stuttgart, Germany. An example motor controller 240 is the model MCDC3006S, and an example gearbox 222 is the model 15/8 gearbox, both also from Dr. Fritz Faulhaber GmbH & Co. KG. In an example, motor 230 has 2,048 clicks per revolution and gearbox 222 has a gear ratio R of 1670:1. The number of clicks per degree is given by 2,048×1,670/360=9,500 clicks/degree. An example angular sweep length is 15 degrees centered on 832 nm. The average wavelength increment per click is 98.2 femtometers, or about 0.0001 nm. In an example, the repeatability of a wavelength sweep is better than a single click.

Figure 15:
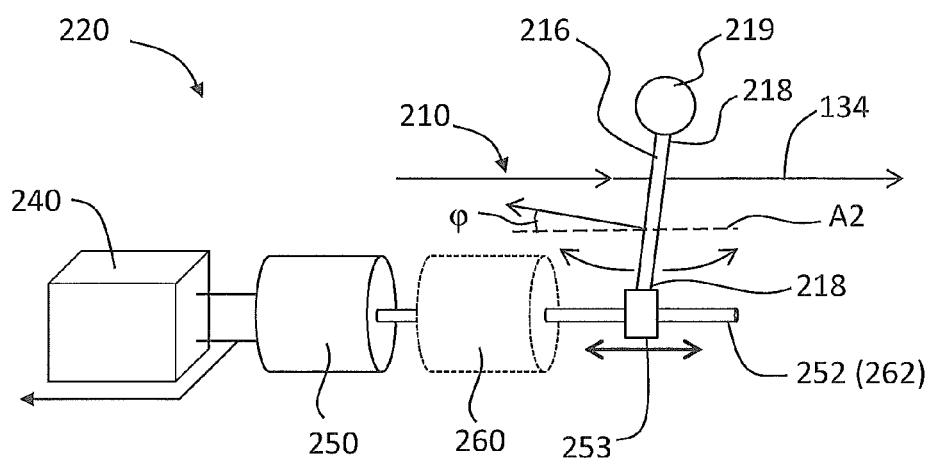
FIG. 15 is similar to FIG. 14 and illustrates another example of an angle-adjustment unit that includes a linear actuator and an angle-adjustable filter that swings on a hinge.

FIG. 15 is a schematic side elevated view of an embodiment of an angle-adjustment unit 220. The angle-adjustment unit 220 includes motor controller 240 electrically connected to a motor 250 that has a screw shaft 252. The screw shaft 252 is mechanically connected to filter 216 at or near one of two filter ends 218 via screw nut 253. A hinge 219 connected to filter 216 at the filter end 218 opposite the filter end 218 to which the screw shaft 252 is connected allows for filter 216 to rotate (swing) as screw shaft 252 is urged to move along its axis by motor 250. In an example, screw shaft 252 may be a ball-screw shaft. A variety of other configurations for angle-adjustment unit 220 that employ different types of adjustment means may also be employed. A gearbox 260 (shown in phantom) with a drive shaft 262 can also be employed to provide improved positional accuracy. In a further example, motor 250, gearbox 260, screw shaft 252 and screw nut 253 may be replaced with a linear stage system containing a linear motor.

With reference to tunable light source system 200 of FIG. 12, in an example, a suitable filter 216 is an interference filter, also known as a dichroic filter. The center wavelength $\lambda_C$ is given by:

$$\lambda_C(\varphi) = \lambda_0 \sqrt{1 - \frac{\sin^2\varphi}{n^2}}$$

where $\phi$ is the aforementioned filter angle and n and $\lambda_0$ are constant properties of filter 216. In one embodiment, filter angle $\phi$ is tuned to 11.5° and within a range of ±7.5° about this angle. The band-pass $\Delta\lambda_T$ of filter 216 can vary slightly with tuning of $\lambda_C$, but in examples the spectral shape is well represented by a Gaussian function or a Sinc function.

As discussed above, there is a need to control the filter angle $\phi$ to a high degree of resolution, such as to $1/3,000^{th}$ of a degree. However, angle-adjustment units having such resolution are expensive (presently greater than $1,000) and are also rather large. Thus, tunable light source system 200 as disclosed herein employs a configuration for angle-adjustment unit 220 that utilizes relatively inexpensive components in combination with an absolute reference measurement rather than employing a single expensive high-resolution encoder.

With reference now also to FIG. 14, angle-adjustment unit 220 employs motor controller 240 and motor 230 having relatively low resolution and low cost (e.g., about 1/5 of a degree, at a present-day cost of about $50) in combination with gearbox 222. The gearbox 222 provides the aforementioned mechanical advantage or gear ratio R, that is, the ratio of motor angular position (x) to filter angle $\phi$.

The filter angle $\phi$ can be expressed as:

$$\varphi = \varphi_{CR} + \frac{x - x_{CR}}{R},$$

The wavelength tuning parameter x is measured relative to some initial condition or position, such as the position at system power-up, $x_{CR}$ is the reference wavelength tuning parameter when detected light spectrum D(x) from the detector is at its maximum, and $\phi_{CR}$ is the reference filter angle corresponding to the peak of the detected light spectrum from photodetector 320.

Factors relating to specific modes of operation such as motor speed and direction (backlash) are omitted for clarity. These factors tend to be insubstantial, especially in the case where reference measurements are carried out in the same manner or at the same time as the actual biosensor 102 measurements.

A change in filter angle φ with respect to wavelength tuning parameter x is a function of the gear ratio, namely:

$$\frac{d\varphi}{dx} = \frac{1}{R}.$$

The gear ratio R is considered to be constant. Wear and tear in gearbox 222 may affect the wavelength tuning parameter x, but not the (average) gear ratio R. The gear ratio R may be a large number (i.e., a "low" gear ratio), e.g., R≥1,000 or even R≥5,000. Then the earlier precision in the wavelength tuning parameter x of $\frac{1}{5}^{th}$ of a degree becomes $\frac{1}{25,000}^{th}$ of a degree for R=5,000. This degree of resolution exceeds the previously stated example resolution requirement of $\frac{1}{3,000}^{th}$ of a degree.

In an example of tunable light source system 200, reference band-pass filter 310 is substantially the same as tunable filter 216, i.e., tunable filter bandwidth $\Delta\lambda_T=\Delta\lambda_R$. This allows for substantially the same signal processing in controller 150 for biosensor 102 measurements and reference measurements. In an example, reference band-pass filter 310 is placed at a reference angle β that is within the range of the filter angle φ, e.g., at an angle that represents the middle of the range. In an example, this mid-range angle is 11.5 degrees.

Figure 16:
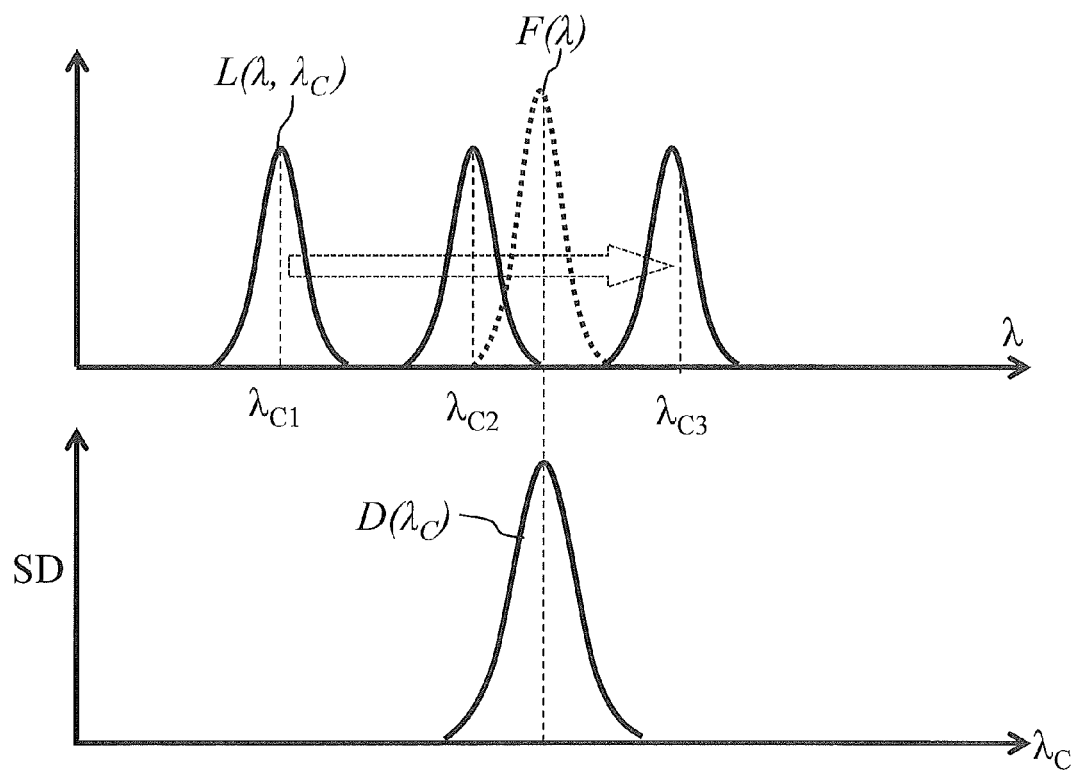
FIG. 16 is similar to FIG. 11 and illustrates an example where the tunable light beam has a Gaussian spectrum, the reference filter has a Gaussian band-pass, and the resulting detected light spectrum has a Gaussian shape.

FIG. 16 shows a plot similar to that shown in FIG. 11 and illustrates an example where the tunable light beam spectrum $L(\lambda, \lambda_C)$ is Gaussian with a width $\Delta\lambda_T=w_L$ and the reference filter transmission spectrum is also Gaussian with a width $\Delta\lambda_R=w_F$. In this case, the equation for detected light spectrum $D(\lambda_C)$ presented above is a convolution and the resulting detected light spectrum $D(\lambda_C)$ has a spectral width $W_D = \sqrt{w_L^2 + w_F^2}$. In the example of an interference filter, the filter transmittance distributions are closely Lorentzian, which has very close to a Gaussian shape near the peak.

Optical Interrogation System Using the Tunable Light Source

The tunable light source 106 having a filter spectral linewidth matched to the biosensor resonance linewidth is suitable for use in swept-wavelength optical readers, including photodiode-based multichannel optical readers and CCD/CMOS-based imaging optical readers. The tunable light source 106 can replace the narrow-band tunable lasers used in prior art optical reader systems. The measured sensor spectrum is the convolution of the relatively wide spectral linewidth of incident beam 134I and the biosensor 102 resonance linewidth, and this operation automatically removes interference fringes from the sensor.

The simplicity and high performance of tunable light source 106 allows for compact imaging systems 114 and thus enables LID optical reader system 100 to be very compact, i.e., to have a small form factor, which in one example is 10 inches by 4 inches by 7 inches. This form factor allows system 100 to fit into a suitcase-sized or briefcase-sized housing, thus making the system easily transportable.

It will be apparent to those skilled in the art that various modifications to the preferred embodiment of the disclosure as described herein can be made without departing from the spirit or scope of the disclosure as defined in the appended claims. Thus, the disclosure covers the modifications and variations provided they come within the scope of the appended claims and the equivalents thereto.

What is claimed is:

1. A tunable light source system that provides a reference to a wavelength tuning parameter, comprising:
   a tunable light source that emits a tunable light beam having a tunable center wavelength $\lambda_C$ that is a function of a wavelength tuning parameter x, the tunable light source generating an electrical signal representative of the wavelength tuning parameter;
   a light-deflecting element disposed in the tunable light beam to deflect at least a portion of the tunable light beam;
   a reference filter having a reference bandwidth and disposed to filter the deflected portion of the tunable light beam to form a filtered light beam;
   at least one photodetector arranged to detect the filtered light beam and generate at least one detector electrical signal representative of a detected light spectrum that has a maximum value; and
   a controller operably connected to the tunable light source and the photo detector and configured to receive the wavelength-tuning-parameter electrical signal and the at least one detector electrical signal and determine a reference wavelength tuning parameter $x_{CR}$ that defines a reference tunable center wavelength $\lambda_{CR}$ a at the maximum value of the detected light spectrum;
   wherein the tunable light source includes an angle-adjustable filter and an angle-adjustment unit operably connected to the angle-adjustable filter to adjust a filter angle of the angle-adjustable filter to tune the tunable center wavelength $\lambda_C$ of the tunable light beam, and the angle-adjustment unit comprises:
   a gear box having a gear ratio and mechanically connected to the angle-adjustable filter;
   a motor mechanically connected to the gear box; and
   a motor controller operably connected to the motor and to the controller.

2. The system of claim 1, further comprising the controller having instructions embodied in a computer-readable medium that cause the controller to calculate the maximum value of the detected light spectrum.

3. The system of claim 1, wherein the angle-adjustable filter has a range of filter angles and wherein the reference filter has a reference angle within the range of filter angles.

4. The system of claim 1, wherein the tunable light source includes a broadband light source having one of a superluminescent diode (SLD) and a light-emitting diode (LED).

5. The system of claim 1, wherein the light-deflecting member includes one of a beam splitter and a mirror.

6. The system of claim 1, wherein the at least one photodetector comprises first and second photodetectors respectively arranged relative to the reference band-pass filter to respectively receive the filtered light beam as a reflected light beam reflected from the reference band-pass filter and a transmitted light beam transmitted by the reference band-pass filter and in response thereto generate first and second detector signals, and wherein the controller is configured to calculate the maximum value of the detected light spectrum based on the first and second detector signals.

7. A label-independent optical reader for reading at least one resonant waveguide grating (RWG) biosensor supported by a microplate, comprising:
   the tunable light source system of claim 1 that emits the tunable light beam over a range of center wavelengths $\lambda_C$;

an illumination system configured to direct the tunable light beam to the at least one RWG biosensor and form a corresponding reflected light beam;

an optical imager arranged to receive the reflected light beam and configured to form therefrom a digital image; and a controller configured to process the digital image to establish a resonant wavelength for the at least one RWG biosensor.

8. The tunable light source system according to claim 1, wherein the maximum value of the detected light spectrum is defined by a parabolic fitted curve.

9. The tunable light source system according to claim 1, wherein the wavelength tuning parameter is a mechanical position, a voltage, or a current.

10. The tunable light source system according to claim 1, wherein the wavelength tuning parameter is the angle-adjustable filter's angle.

* * * * *